US012569122B2

(12) United States Patent
Seibt et al.

(10) Patent No.: US 12,569,122 B2
(45) Date of Patent: Mar. 10, 2026

(54) ADAPTABLE WORKING CHANNEL APPARATUS, TISSUE-CLIP APPLICATION ADAPTER AND SURGICAL EQUIPPING SYSTEM

(71) Applicant: Ovesco Endoscopy AG, Tübingen (DE)

(72) Inventors: Michael Seibt, Tübingen (DE);
Antonio Caputo, Dettenhausen (DE);
Nico Hofmann, Wernau (DE);
Chi-Nghia Ho, Reutlingen (DE)

(73) Assignee: Ovesco Endoscopy AG, Tübingen (DE)

( * ) Notice: Subject to any disclaimer, the term of this patent is extended or adjusted under 35 U.S.C. 154(b) by 299 days.

(21) Appl. No.: 18/273,409

(22) PCT Filed: Jan. 20, 2022

(86) PCT No.: PCT/EP2022/051233
§ 371 (c)(1),
(2) Date: Jul. 20, 2023

(87) PCT Pub. No.: WO2022/157244
PCT Pub. Date: Jul. 28, 2022

(65) Prior Publication Data
US 2024/0115115 A1     Apr. 11, 2024

(30) Foreign Application Priority Data
Jan. 21, 2021    (DE) ......................... 102021101273.2

(51) Int. Cl.
*A61B 1/00*      (2006.01)
*A61B 1/005*     (2006.01)
*A61B 1/018*     (2006.01)
(52) U.S. Cl.
CPC ........ *A61B 1/0014* (2013.01); *A61B 1/00128* (2013.01); *A61B 1/0052* (2013.01); *A61B 1/018* (2013.01)

(58) Field of Classification Search
CPC . A61B 1/0014; A61B 1/00128; A61B 1/0052; A61B 1/018; A61B 1/012
See application file for complete search history.

(56) References Cited

U.S. PATENT DOCUMENTS

2011/0099773 A1* 5/2011 Golden .............. A61B 1/00128
                                                      24/457
2013/0310641 A1   11/2013 Terliuc et al.
(Continued)

FOREIGN PATENT DOCUMENTS

DE      102009014178 A1     9/2010
DE      102017107546 A1     10/2018
(Continued)

OTHER PUBLICATIONS

English Translation of the Written Opinion for International Application No. PCT/EP2022/051233, dated May 6, 2022, 6 pages.
(Continued)

*Primary Examiner* — Amit Chatly
(74) *Attorney, Agent, or Firm* — Buchanan Ingersoll & Rooney PC

(57)           ABSTRACT

An adaptable working-channel apparatus comprising: at an external working channel attached at its proximal end to a first mounting coupling; a handle-mounting sleeve for surrounding an endoscope shaft or handle, and having on its radially outer peripheral side at least one second mounting coupling for releasable mounting engagement with the first mounting coupling. The first mounting coupling comprises two spring-loaded clamping branches that are hinged together like a clothes pin and each form a clamping portion and an actuation portion. The second mounting coupling has a mounting rail extending in the longitudinal direction of the handle-mounting sleeve and has or forms at least one undercut that can be interlockingly clasped by the clamping branches of the first mounting coupling. Also provided is a
(Continued)

distal tissue-clip application adapter that is connectable to the adaptable working-channel apparatus; and a surgical equipping system, having the working-channel apparatus and tissue-clip application adapter.

19 Claims, 3 Drawing Sheets

(56)                 References Cited

U.S. PATENT DOCUMENTS

| 2016/0228113 A1 | 8/2016 | Weitzner et al. | |
|---|---|---|---|
| 2019/0183471 A1* | 6/2019 | LaBombard | A61B 17/068 |
| 2020/0046201 A1 | 2/2020 | Ho et al. | |
| 2021/0052141 A1 | 2/2021 | Schurr et al. | |
| 2023/0172436 A1* | 6/2023 | Chu | A61B 1/2676 |
| | | | 600/104 |

FOREIGN PATENT DOCUMENTS

| DE | 102017112896 A1 | 12/2018 |
|---|---|---|
| JP | 2011152305 A | 8/2011 |
| WO | 2008098124 A1 | 8/2008 |
| WO | 2018012039 A1 | 1/2018 |
| WO | 2018229047 A1 | 12/2018 |

OTHER PUBLICATIONS

German Search Report for German Application No. 10 2021 101 273.2, dated Oct. 11, 2021, with partial translation, 12 pages.

International Search Report and Written Opinion for Application No. PCT/EP2022/051233, dated May 6, 2022, 10 pages.

Office Action (Notice of Reasons for Refusal) issued Nov. 11, 2025, by the Japan Patent Office in corresponding Japanese Patent Application No. 2023-544352 and an English translation of the Office Action. (5 pages).

* cited by examiner

ADAPTABLE WORKING CHANNEL APPARATUS, TISSUE-CLIP APPLICATION ADAPTER AND SURGICAL EQUIPPING SYSTEM

This application is a U.S. National Phase application of PCT International Application No. PCT/EP2022/051233, filed Jan. 20, 2022, which claims the benefit of DE 102021101273.2, filed Jan. 21, 2021, both of which are incorporated by reference herein.

The present disclosure relates to an adaptable working channel apparatus for adaptive mounting to an endoscope having at least one external working channel connected at its proximal end portion to a first mounting coupling, a handle-mounting sleeve formed separately from the working channel and provided to encompass an endoscope shaft or an endoscope handle like a sleeve and having at its radially outer circumferential side at least one second mounting coupling configured to come into releasable mounting engagement with the first mounting coupling. Furthermore, the present disclosure relates to a distal tissue-clip application adapter and a surgical equipping system for an endoscope having the adaptable working channel apparatus and the tissue-clip application adapter.

PRIOR ART

Medical endoscopes are used for many different patient procedures and are therefore subject to a wide range of requirements. In order to meet the needs of the large number of different, highly specialized procedures, there are highly specialized endoscopes and/or adapter systems for additional working channels, which enable additional instruments and/or functionalities to be provided. Such adapter systems are configured for being equipped to standard endoscopes in particular. They have to be quickly and easily attachable to the endoscope and have to be securely attached to it. Preferably, they can be manufactured inexpensively as disposable parts and are thus simple to construct.

An example of an additional tube assembly that can be coupled to an endoscope handle via a proximal connector can be found in DE 10 2009 014 178 A1. This document discloses a clamping bush that can be clamped to an endoscope handle and has a bracket gap with a nub, and an external working channel that has wings for mounting on the bracket gap with an engagement recess for engaging with the nub. However, this connection is either tight and thus difficult and possibly jerky to operate, or smooth and unstable. Furthermore, since a counter-pressure has to be built up when connecting, two hands are required to attach the external working channel to the endoscope handle. In addition, the rotating ring may wear out and cause further instability. However, for many patient treatments or operations, both high stability of the connection and easy and safe assembly and disassembly are required.

Furthermore, adapter systems known from the prior art often do not meet the requirements defined by specialized procedures. For example, an adapter system for a distal endoscope tip is known from document DE 10 2017 112 896 A1, which has an attachment with a tissue clip carried thereon that can be pushed down. However, this attachment is severely limited in its possible applications. Furthermore, it has been found that this adapter system can be problematic, for example, when creating an artificial anastomosis (i.e., when creating a connection between two anatomical cavities, such as between the stomach and small intestine). In particular, in a surgically created anastomosis, it may occur that one opening of the connection may be too large. Thus, in the case of an anastomosis of stomach and small intestine, food, for example, may be transported further within the digestive tract too quickly and thus correspondingly inadequately digested. On the other hand, the opening may be too small. In this case, food may be transported too slowly. In both cases, this can lead to digestive problems.

SUMMARY OF THE INVENTION

The object underlying the present disclosure is to improve or eliminate disadvantages of the prior art. In particular, an adaptable working channel system and/or a tissue-clip application adapter and/or a surgical equipping system for an endoscope should be provided that is simple, inexpensive and safe to assemble and disassemble and/or can reliably and easily provide additional functionalities.

The object underlying the disclosure is solved by an adaptable working channel apparatus having the features of claim 1.

More specifically, the object underlying the invention is solved by an adaptable working channel apparatus for adaptive mounting to an endoscope. The adaptable working channel apparatus has at least one external working channel connected at its proximal end portion to a first mounting coupling. Furthermore, the adaptable working channel apparatus has a handle-mounting sleeve formed separately from the working channel and provided to encompass an endoscope shaft or an endoscope handle like a sleeve. On the radially outer circumferential side of the handle-mounting sleeve, at least a second mounting coupling is provided, which is configured to come into a releasable mounting engagement with the first mounting coupling. The first mounting coupling has two clamping branches spring-loaded into a clamping engagement, hinged together in a clothespin-like manner to form a respective clamping-branch portion and a manual actuation branch portion. The second mounting coupling has a mounting rail extending in the longitudinal direction of the handle-mounting sleeve and at least one undercut. The undercut is dimensioned such that it can be form-fittingly embraced by the clamping branches of the first mounting coupling. The adaptable working channel apparatus advantageously enables a simple, jerk-free and stable coupling of an external working channel to an endoscope handle.

In other words, an adaptable working channel apparatus is provided with an external working channel that is selectively attachable or detachable to an endoscope handle via a simple mounting system. Accordingly, the (external) working channel and a handle-mounting sleeve attachable to the endoscope handle have a first and a second mounting coupling configured to be releasably coupled to each other. The first mounting device on the working channel forms a clamp with two clamping branches that are elastically adjustable in angle to each other via a rocker joint (i.e., connected like a clothes pin). The clamping branches each have a first free end that protrudes beyond the rocker joint on a clamping side to form a clamping-branch portion with at least a first engagement element, such as a protrusion or an opening. A second free end of the clamping branches forms an actuation branch portion configured for opening the opposing clamping-branch portions by a user via a manual push actuation, and being opposite the clamping-branch portion with respect to the rocker joint. The second mounting coupling has a clasp-shaped or bush-shaped portion that can be snapped/attached around the endoscope handle or shaft. The clasp-shaped or bush-shaped portion has longitudinal bars/mounting rails with at least one second engagement element in the form of an opening or projection provided for engagement with a compatible first engagement element of the clamping branch(es). The clamping-branch portion and the actuation branch portion of the respective clamping branches are in particular rigidly connected to each other.

Advantageous embodiments are the subject matter of the dependent claims and are described in more detail below.

The rocker joint or hinge may be provided directly on the working channel or respectively on a connection bush of the working channel or may be spaced in the radial direction with respect to the working channel via a spacer. Such a spacer can ensure that a proximal access to the working channel is spaced from the endoscope in such a way that it is easily accessible. Furthermore, the actuation branch portions are preferably arranged such that they can be operated with one hand for opening and/or closing.

The clamping branches of the first mounting coupling preferably form engagement elements facing each other at their clamping-branch portions, such as hook-shaped protrusions or openings, which are configured to engage behind the at least one undercut of the second mounting coupling. In particular, contact surfaces of the undercut and of the engagement elements can be formed extending perpendicularly to the clamping branches, so that a stable contact is created between the mounting couplings. In particular, this is possible since the hinging in a clothespin-like manner causes the two clamping branches to perform a sweeping movement, so that the respective engagement elements perform a large transverse movement and thus the engagement elements can have a relatively large extension transverse to the longitudinal direction of the clamping branch in order to provide relatively large contact/attachment surfaces of this kind. It is particularly preferred if the protrusions are formed along an entire width of the respective clamping-branch portions in order to provide the longest possible and thus stable engagement edge.

It has also proved practical for the free ends of the clamping-branch portions to be chamfered at their facing edges to form an insertion wedge between them.

Preferably, at least two undercuts are provided, which are arranged opposite each other on both circumferentially facing side flanks of the mounting rail. The undercut(s) is/are each preferably configured as a through opening which extends tangentially to the longitudinal direction of the handle-mounting sleeve through the handle-mounting sleeve. This is easy to manufacture and provides a particularly stable coupling structure. Preferably, the handle-mounting sleeve may have a substantially cylindrical or conic section-like shape which bulges radially outward to form the mounting rail. In this way, a simple structure is achieved and the handle-mounting sleeve is easy and inexpensive to manufacture.

Further preferably, the clamping-branch portions extend obliquely away from each other from the hinge or rocker joint, respectively. In other words, they enclose an acute angle between them. Accordingly, the clamping-branch portions can also grip around a mounting rail, which is particularly wide and stable. Anti-slip structures, such as grooves or webs, can be formed on the outside of the actuation branch portions (i.e., facing away from each other) to provide a more secure grip during manual actuation of the actuation branch portions.

It has proven practical if the first mounting coupling forms a connection bush, to the distal end of which the working channel is connected. Preferably, a Luer adapter or Luer lock adapter is furthermore connected to a proximal end of the connection bush. The Luer (lock) adapter may be equipped with a biopsy valve. Alternatively, the connection bush can form an integral biopsy valve. This makes it possible, for example, to seal off the external working channel during biopsy or flushing and extends the possible functionalities of the present adaptable working channel apparatus. In particular, the connection bush forms a longitudinal passage/channel connecting the working channel to a proximal inlet port of the connection bush.

Preferably, the clamping branches are respectively elastically connected to each other at a position between the clamping branch portion and the actuation branch portion of the corresponding clamping branch via a connecting web that runs obliquely or perpendicularly to the clamping branches. On the one hand, such a connecting web enables a simple and one-piece, assembly-free configuration of the hinge or rocker joint that connects the two clamping branches to each other. Furthermore, the connecting web can space the two clamping branches from each other. This allows greater actuation travel when opening and closing the clamping branches via actuation of the actuation branch portions.

Further preferably, the connecting web is connected to the connection bush e.g. via a central beam as a spacer, which is centrally attached to the connecting web. A length of the spacer is preferably dimensioned in such a way that it distances the connecting web from the connection bush in order to be able to freely actuate the actuating portions unhindered by the connection bush. Furthermore, a length of the spacer is dimensioned such that a free end of the actuation branch portions is close to the connection bush such that a user can reach around the connection bush to the actuation branch portions with one hand. The spacer can serve as an end stop for the actuation branch portions to prevent excessive actuation and resulting damage to the first mounting coupling.

Conveniently, the clamping branches and the connection bush may be oriented with respect to each other such that a longitudinal axis of the connection bush and a longitudinal axis of the handle adapter sleeve are oriented obliquely with respect to each other in a state in which the first and second mounting couplings are coupled. Preferably, these longitudinal axes include between them an angle of preferably 10° to 50°, more preferably 20° to 25°. Thus, a proximal working channel access is oriented facing away from the endoscope. The proximal working channel access is thus more easily accessible for a user. In particular, this is advantageous in combination with the spacer described above, since the angled arrangement of the connection bush allows the working channel to be guided from a maximum distance diagonally toward the endoscope shaft. In particular, the working channel is attached to the outside of the endoscope shaft and guided in the distal direction.

According to an advantageous aspect, the connecting web is wider than the clamping branches such that it protrudes laterally (i.e., in a proximal and/or distal direction or in a longitudinal direction with respect to the working channel) beyond the clamping branches. It is particularly advantageous if, furthermore, the handle-mounting sleeve forms at least two support edges extending transversely to its longitudinal direction and spaced apart in the longitudinal direction, the distance between them corresponding substantially to a width of the connecting web. The undercut is preferably formed between the support edges. In this way, forces that are transmitted via the first and second mounting couplings can be distributed to different coupling elements. For example, forces acting in the longitudinal direction of the working channel or the mounting sleeve can be transmitted via the support edges and lateral edges of the connecting web, and do not load the clamping-branch portions. In this case, the clamping-branch portions only transmit forces acting in the radial direction between the first and second mounting portions.

Preferably, the mounting rail of the handle-mounting sleeve forms a plurality undercuts that are arranged offset to each other in the longitudinal direction. This makes it possible to provide working channels of different lengths, each of which can be combined with the same handle-mounting sleeve. More specifically, for example, a relatively short working channel can be attached to the handle-mounting sleeve via a more distally located undercut and/or a relatively long working channel can be attached via a more proximally located undercut. This simplifies the combination of the adaptable working channel apparatus with endoscopes of different lengths.

Advantageously, the handle-mounting sleeve forms a plurality of mounting rails that are arranged offset from each other in a circumferential direction of the handle-mounting sleeve, preferably diametrically opposite each other. This enables a more flexible arrangement of the working channel on the endoscope. Furthermore, the adaptable working channel apparatus can thus have several working channels with corresponding first mounting couplings.

According to a further preferred aspect, the handle-mounting sleeve has a receiving opening configured to receive a radial protrusion of the endoscope handle. The radial protrusion is, for example, an exit of an endoscope-integrated, internal working channel on the endoscope handle. Thus, the handle-mounting sleeve is form-fittingly fixed to the endoscope handle at least in the longitudinal direction and/or in the circumferential direction of the handle adapter sleeve. This enables a particularly simple and stable, wear-resistant connection between the handle-mounting sleeve and the endoscope handle.

Furthermore, it is advantageous if the handle-mounting sleeve has a continuous longitudinal gap and is at least partially elastic, such that the handle-mounting sleeve can be snapped onto the endoscope shaft/handle in a clasp-like manner. This allows the handle-mounting sleeve to apply a clamping force to the endoscope shaft/handle. In particular, a circumferential region of the handle-mounting sleeve opposite the longitudinal gap may include one or more apertures to form an at least partially resilient region. In other words, a sleeve structure may be locally weakened to have a higher elasticity than other regions of the handle-mounting sleeve. Particularly advantageously, the longitudinal gap is formed on a diametrically opposite side of the receiving opening, and the weakened sleeve structure is provided by the receiving opening.

According to a further advantageous aspect, the handle-mounting sleeve comprises a strap holder to which a first end of a closure strap is attached or attachable. Furthermore, the handle-mounting sleeve may comprise a strap fixing portion configured to hold a closure portion of the closure strap in a position in which it is wrapped around the handle-mounting sleeve such that it extends across the longitudinal gap. In other words, a closure strap is provided which is disposed on the handle-mounting sleeve such that it encompasses the longitudinal gap and at least a part of the handle-mounting sleeve to apply tension to an endoscope portion disposed within the handle-mounting sleeve. Preferably, the strap holder and/or the strap fixing portion is attached radially outward to one or, correspondingly, to two opposite mounting rails. Thus, a lever is provided which allows to apply a higher clamping force of the closure strap around the handle-mounting sleeve. The closure portion may, for example, be configured as a ratchet strap, according to a perforated belt principle or made of Velcro, wherein the strap fixing portion is to be adapted accordingly.

Alternatively or additionally, the object underlying the disclosure is solved by a tissue-clip application adapter according to claim 10.

More specifically, a tissue-clip application adapter is provided which is configured in the manner of a cap attachment for a medical endoscope, i.e. separately therefrom. The tissue-clip application adapter has a bush-like base body. The base body has a proximal endoscope holding portion configured to be attached to a distal head of the medical endoscope. Furthermore, the base body has a tissue-clip holding portion configured to support a tissue clip on its radially outer circumferential surface such that the tissue clip is removable in the distal direction from the tissue-clip holding portion. In particular, the base body is open in the distal direction to allow instruments or the like to be advanced through the base body to a treatment site/into a cavity of a patient and/or to allow patient tissue to be retrieved/drawn into the base body.

The tissue-clip application adapter furthermore comprises a first adapter-integrated working-channel terminal having a first inner channel. The first inner channel extends through the base body such that its proximal first channel end opens at an exterior of the base body and that its distal first channel end opens into an interior within the base body. In other words, a through passage to which a separate working channel is or can be connected extends from a proximal direction from radially outside the base body diagonally, i.e. in a distal and radially inner direction, continuously through a wall of the base body. Optionally, an inner flange may be provided within the second inner channel in order to fix the position of an external working channel connected or, respectively, to be connected in the distal direction.

This has the advantage that an additional working channel can be provided through which instruments, irrigation tubes or similar items can be advanced to a space directly in front of the actual endoscope. In particular, inserted instruments etc. are already oriented in a corresponding radial direction due to the diagonal course of the first inner channel, which can be advantageous, for example, for rinsing processes or for drawing tissue into the base body.

In particular, this is advantageous for defined, targeted placement of a tissue clip. For this purpose, a gripping instrument can be advanced through the corresponding external working channel and the first inner channel into the base body and can emerge distally from the base body. There, it can selectively grip patient tissue in an area that lies directly in the field of view of an optic system of the endoscope and pull it into the interior of the base body. If the tissue clip is then removed/pushed down in the distal direction from the tissue-clip holding portion, a targeted, defined clamping of a specific portion of patient tissue takes place. The gripping instrument may be a mechanical, e.g. forceps-like, instrument or a suction instrument that can hold/grip the patient tissue via suction pressure.

A second adapter-integrated working-channel terminal of the tissue-clip application adapter has a second inner channel extending along the base body such that a proximal second channel end and a distal second channel end of the second inner channel open at an outer side of the base body. Furthermore, the distal second channel end is disposed proximal to the tissue-clip holding portion. In other words, an (inner) channel extending substantially linearly along an outer circumferential surface of the bush-like base body is provided for connecting (independently of the first inner channel) a further external working channel connected or connectable to the tissue-clip application adapter coming from a proximal direction. Optionally, a flange may be provided within the second inner channel to fix the position of an external working channel in the distal direction, said external working channel being connected or, respectively, to be connected.

Thus, the present tissue-clip application adapter makes it possible to provide instruments, irrigation tubes, special optic system, etc. that can observe or manipulate an environment of the patient tissue to be clamped without limiting the functionality of the tissue-clip application adapter for clamping patient tissue via the tissue clip or without significantly limiting the adapted endoscope. This is advantageous in particular when performing an anastomosis in which a tissue opening of defined size is to remain open adjacent to the tissue to be clamped by the tissue clip.

In this application example of anastomosis placement, for example, a spreading instrument, such as a balloon catheter, can be advanced through the correspondingly connected external working channel and the second inner channel into the tissue opening to be provided. There, the spreading instrument can be expanded to a predetermined size/diameter. If the patient tissue to be stapled is then grasped directly next to the spreading instrument, e.g. as described above, by a gripping instrument and pulled into the base body, the patient tissue is stretched around the spreading instrument. When the staple is subsequently set and the spreading instrument is removed, a tissue opening remains adjacent to the clasped tissue site, which corresponds substantially to the predetermined size/diameter of the spreading instrument when spread.

Preferably, a sliding bush is mounted is mounted in a longitudinally slidable manner on the base body immediately proximal to the tissue clip holding portion as a tissue clip push-off device for sliding the tissue clip distally off the tissue clip holding portion. In other words, a sliding bush is provided for pushing off the tissue clip between the tissue-clip holding portion and the distal end of the second inner channel. This allows for a particularly easy, uniform and effective sliding off of the tissue clip. Furthermore, since the sliding bush requires only a small amount of radial installation space, the tissue clip push-off device and the spreader device, for example, cannot get in each other's way.

According to an advantageous aspect, a distal front edge of the base body (i.e., a most distal end of the tissue-clip application adapter) has two recesses which are (preferably diametrically) opposite to each other and which extend or are recessed in a proximal direction. In other words, the front edge is jaw-like in shape, wherein the recesses form mouth corners of the jaw-like shape. This is advantageous in particular in order to be able to pull the patient tissue in a particularly defined manner into the base body and thereby fold it into the recesses. This enables a particularly defined, longitudinally directed clamping of the patient tissue.

Particularly preferably, the recesses are each arranged offset from the second adapter-integrated working-channel terminal in opposite circumferential directions of the base body, preferably by 70° to 110°, and further preferably by 90°. That is, one of the recesses is offset in a first circumferential direction by a corresponding angle to the second working-channel terminal and the respective other recess is offset by a corresponding angle in the opposite circumferential direction to the second working-channel terminal. Thus, the two recesses are substantially diametrically opposed and the second working-channel terminal is disposed at a circumferential position between the two recesses. In other words, the second working-channel terminal and the recesses are oriented with respect to each other such that when operating an anastomosis, the patient tissue to be stapled is folded substantially tangentially to a tissue opening to be provided. Subsequent stapling of the tissue is thus particularly precise and targeted.

It is further advantageous if the tissue-clip holding portion forms two diametrically opposed spread support surfaces configured to hold the tissue clip spread open in a predetermined pose, wherein one of the spread support surfaces is aligned with the second adapter-integrated working-channel terminal or at an identical circumferential position of the base body, respectively. In other words, a tissue clip for which the tissue-clip holding portion is adapted is bear-trap shaped and has two jaw-like claw portions oriented distally. One of the claw portions is located at the same circumferential position as the second working-channel terminal. This is advantageous because, when operating on an anastomosis, one of the claw portions, which is configured to firmly grip and claw the patient tissue to be clamped, thus engages the patient tissue immediately adjacent to the tissue opening to be provided. In this way, an amount of 'loose' tissue remaining between the tissue opening and the stapling, which can lead to inaccuracies in setting a size of the tissue opening, can be minimized and digestive discomfort of the patient can be avoided.

Alternatively or additionally, the object underlying the disclosure is solved by a surgical equipping system according to claim 15.

More specifically, a surgical equipping system for an endoscope having an adaptable working channel apparatus described above and a tissue-clip application adapter described above is provided. The first adapter-integrated working-channel terminal is coupled to a distal end portion of the external working channel of the adaptable working channel apparatus as a first external working channel. Furthermore, the equipping system comprises a gripping instrument inserted or configured to be inserted distally through the first external working channel. Thus, the gripping instrument is advanceable through the interior of the base body of the tissue-clip application adapter.

Furthermore, a second external working channel is provided which is connected at its proximal end portion to a third mounting coupling for mounting to the handle-mounting sleeve of the adaptable working channel apparatus. A distal end portion of the second working channel is coupled to the second adapter-integrated working-channel terminal of the tissue-clip application adapter. Furthermore, the equipping system comprises a spreading instrument, in particular a balloon catheter, which is inserted or configured to be inserted into the second external working channel in a distal direction. Thus, the spreading instrument is providable radially outside the base body of the tissue-clip application adapter. This equipping system can advantageously achieve an optimal setting of a remaining tissue opening in an anastomosis, as described in more detail above. Preferably, the first and the second working channel as well as the respective first mounting couplings are marked differently, for example in different colors, in order to distinguish the working channels.

In summary, the object underlying the invention is solved as follows. The gripping handle (handle-mounting sleeve) may have several functions. In one aspect, it is preferably constructed like a clasp that can be easily slid onto or respectively pulled off of the endoscope (in particular endoscope handle). By this design, the gripping handle can have a retaining force on the endoscope handle by clamping it on. Furthermore, this design also allows for different shapes of endoscope handles to be accommodated. In particular, an opening in the center (a central region) of the gripping handle allows positioning directly at the entrance of an internal working channel of the endoscope (the opening may be placed around the entrance). Hereby, the gripping handle is positioned in height (or axial extension) (fixed in position in proximal-distal direction). Furthermore, a fixing strap (closure strap) can be used/provided to attach the gripping handle in its entirety to the endoscope/endoscope handle.

Furthermore, the gripping handle preferably has six (longitudinally and/or circumferentially distributed) latching positions to which a connector (first mounting coupling) can be attached. The different positions are intended to compensate for the different endoscope lengths (i.e., depending on the length of the endoscope to be adapted, a different locking position is selected relative to the axial extension of the gripping handle) and also to enable the user to follow his/her own preferences.

The connector is (forms) an input for an external tube (working channel) and is practically configured with a LuerLock (Luer adapter). A (Pentax) biopsy valve, for example, can be placed on this LuerLock. The connector is preferably attached to the gripping handle by snap hooks (engagement elements of the first mounting coupling or clamping-branch portions, respectively). The fastening should be designed to be intuitive and simple. Furthermore, the attachment/connection of the gripping handle and the connector can be opened via (preferably ribbed) wings (actuation branch portions) in order to be able to reposition the connector.

In summary, the connector may include a Luer lock, optionally a biopsy valve that is preferably attachable to the Luer lock, an attachment for a BARS system (i.e., tissue clip application adapter) and/or an additional working channel (AWC system, 'Additional Working Channel'). The attachment may be integrated onto BARS/AWC as part with (i.e., form an integral system). In addition, the connector may have actuation clamping branches (i.e., the wing or actuation branch portions, respectively).

FIGURE DESCRIPTION

The present disclosure is described below with reference to preferred embodiments. However, these are only illustrative in nature and are not intended to limit the scope of protection of the present invention. Furthermore, in describing the various embodiments, the same reference signs are used for the same components in order to avoid redundant descriptions of them.

Figure 1:
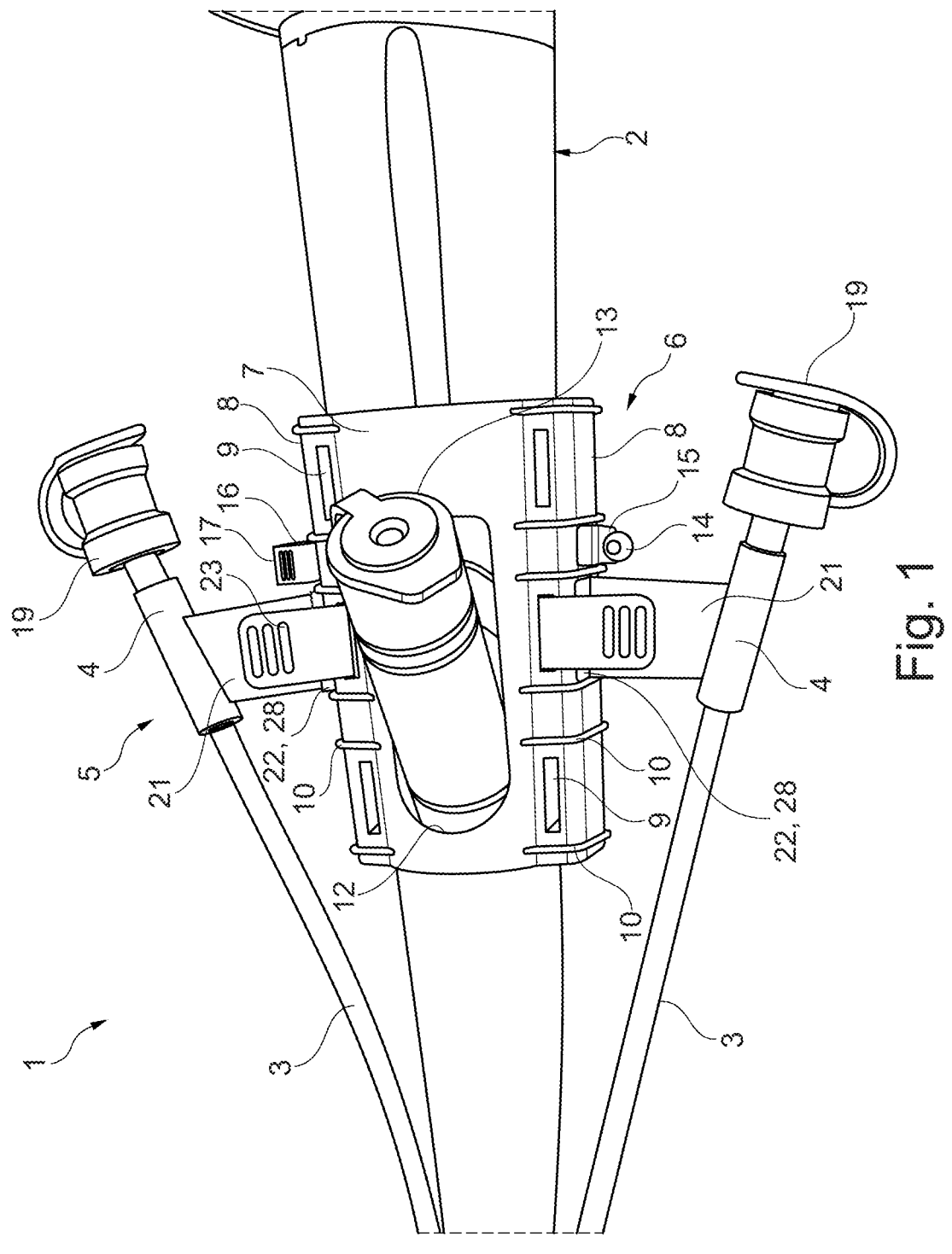
FIG. 1 shows an endoscope with an adaptable working channel apparatus fixed thereto according to a first aspect or a preferred embodiment.

FIG. 1 shows an adaptable working channel apparatus 1 which enables a medical endoscope 2 to be equipped or retrofitted with at least one external working channel 3. In this embodiment, two (identical) working channels 3 are provided as an example. The working channels 3 are each formed separately from the endoscope 2. Each external working channel 3 has a proximal end portion (i.e., facing a user or facing away from a patient, respectively). This proximal end portion is connected to a connection bush 4 of a first mounting coupling 5. The first mounting coupling 5 is configured to come into releasable holding engagement with a second mounting coupling 6, which is attached to the endoscope 2 and is described in more detail below.

Figures 2, 3, 4:
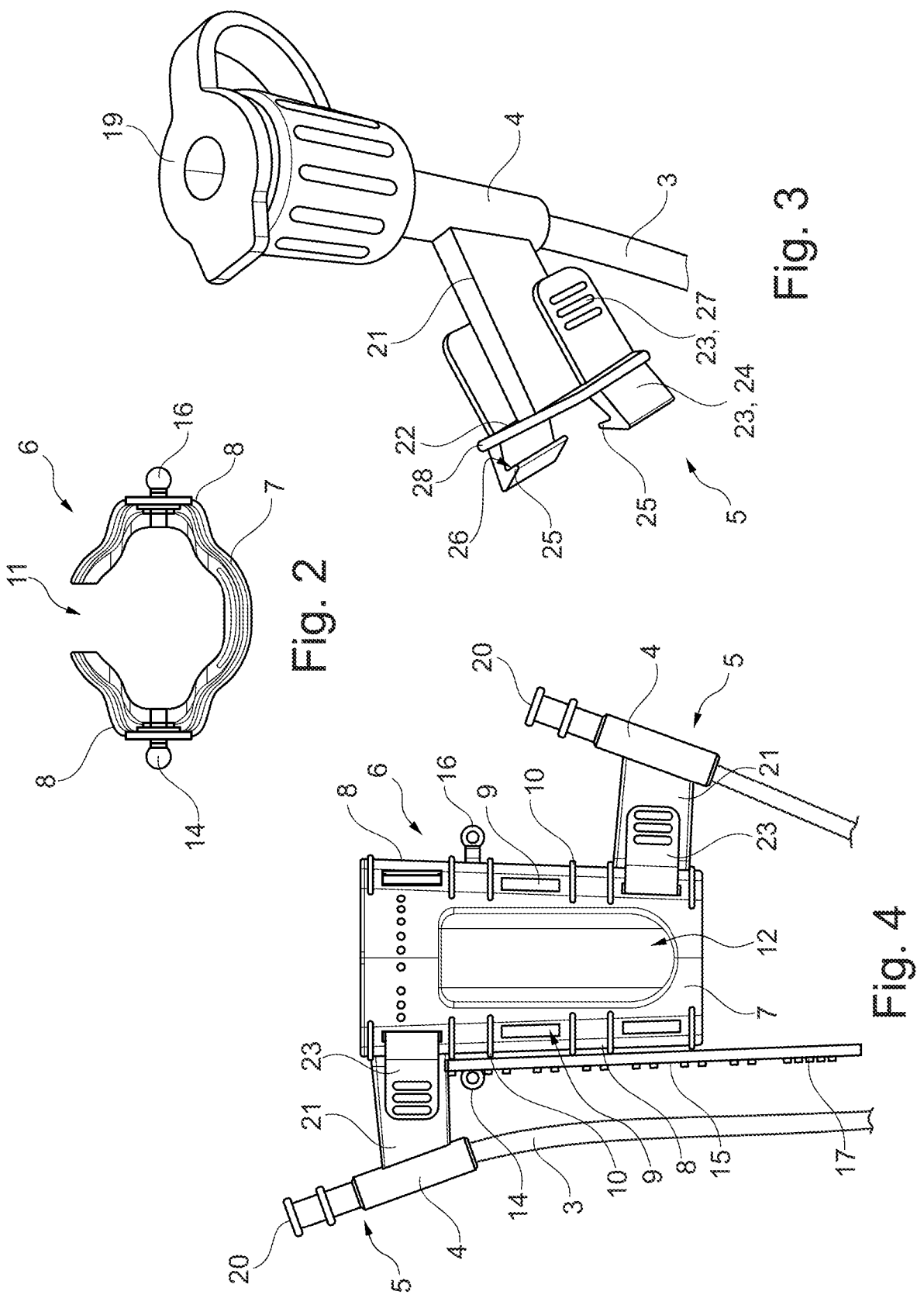
FIG. 2 shows a top view of a handle-mounting sleeve of the adaptable working channel apparatus according to the preferred embodiment.
FIG. 3 shows a perspective view of a connector of the adaptable working channel apparatus.
FIG. 4 shows an adjustable configuration of the adaptable working channel apparatus according to the first embodiment.

The second mounting coupling 6 is formed on a radially outer side of a handle-mounting sleeve 7. The handle-mounting sleeve 7 is substantially bush-like or clasp-like and surrounds a portion of the endoscope 2, in particular, as shown in FIG. 1, the endoscope handle. The handle-mounting sleeve 7 forms a mounting rail 8 projecting radially outward and extending in the longitudinal direction of the handle-mounting sleeve 7. In this embodiment, two (identical) mounting rails 8 are provided opposite each other. FIG. 2 shows a top view of the handle-mounting sleeve 7 from a proximal direction, in which it is clearly visible that the mounting rails 8 are formed in the form of bulges of a circumferential wall of the handle-mounting rail 8.

The mounting rails 8 have access openings 9 on their flanks or, respectively, on their sides, which are oriented in a circumferential direction of the handle adapter sleeve 7. The access openings 9 are configured/dimensioned for engagement with the first mounting coupling 5. In particular, the access openings 9 extend continuously throughout the mounting rail 8 to open on both flanks of the mounting rail 8. The mounting rails 8 further form support edges 10 which extend in a direction transverse, in particular orthogonal, to the longitudinal direction of the handle-mounting sleeve 7. The support edges 10 are arranged in such a way that one of the support edges 10 is located on each side of each access opening 9, as viewed in the longitudinal direction.

The handle-mounting sleeve 7 has a longitudinal gap 11 shown in FIG. 2, which completely breaks/splits the handle-mounting sleeve 7 along its longitudinal direction at a circumferential position. Thus, the handle-mounting sleeve 7 can be widened to receive the endoscope handle through the longitudinal gap 11 and can be snapped thereon. The handle-mounting sleeve 7 has, in particular on a side opposite the longitudinal gap 11, a receiving opening 12, which is configured to receive a radial protrusion 13 of the endoscope.

Furthermore, in an area between two support edges 10, where preferably none of the access openings 9 is provided, a strap holder 14 for holding a closure strap 15 is formed on a radial outer side of one of the mounting rails 8. Preferably, the closure strap 15 is translationally fixed to the strap holder 14, but optionally rotatable about an axis transverse to the longitudinal direction of the handle-mounting sleeve 7. At the same height with respect to the longitudinal direction, a strap fixing portion 16 is formed on the opposite mounting rail 8. The strap fixing portion 16 is configured in such a way that a closure portion 17 of the closure strap 15 can be fastened thereto when it is wrapped around the handle-mounting sleeve 7 spanning the longitudinal gap 11. In FIG. 1, the closure strap 15 is shown in such an attached position spanning the longitudinal gap, wherein only ends of the closure strap 15 are visible, which are respectively held to the strap holder 14 and the strap fixing portion 16 and protrude behind the endoscope. In FIG. 4, the closure strap 15 is shown in a suspended position in which it is not attached to the strap fixing portion. As can be seen in particular from FIG. 2, the strap fixing portion 13 and/or the strap holder 14 may be provided in the form of buttons.

The structure of the first mounting coupling 5 is clearly visible in particular in FIG. 1 and FIG. 3. More precisely, the first mounting coupling has the connection bush 4, to the distal end of which the external working channel 3 is connected. At the proximal end of the connection bush 4, a biopsy valve 19 is provided according to the configuration shown. Alternatively or additionally, a Luer adapter 20 can be formed, as shown in FIG. 4.

Laterally on the connection bush 4, a beam-like spacer 21 extends radially outward and preferably distally to provide an inclined arrangement of the working channel 3 and of the handle-mounting sleeve 7 when the first and second mounting couplings 5, 6 are connected to each other. At an end of the spacer 21 facing away from the connection bush 4, a connecting web 22 is arranged which extends in both directions transversely to the spacer 21. That is, the spacer 21 and the connecting web 22 are T-shaped. At outer ends of the connecting web 22, a clamping branch 23 is formed in each case, which extends at least in sections substantially transversely to the connecting web 22 or substantially parallel to the spacer 21. The connecting web 22 provides a rocker joint around which the clamping branches 23 are elastically angularly adjustable relative to each other.

The clamping branches 23 project in a direction away from the connection bush 4 (i.e. radially outward with respect to the connection bush 4) beyond the rocker joint or connecting web 22 to form clamping-branch portions 24. The clamping-branch portions 24 are angled slightly outward, i.e., away from each other. Furthermore, the clamping-branch portions 24 each form a hook-shaped protrusion 25 facing the corresponding other clamping-branch portion 24 and configured to engage the access openings 9 of the second assembly device 6. In a rest position, the clamping branches 23 are in a closed position, in which the clamping-branch portions 24 are moved toward each other, preferably maximally. A contact surface 26 of the respective protrusion 25 facing the connection bush 4 comes into contact with a corresponding contact surface of one of the access openings 9 of the second assembly device 6 when the first and second assembly devices 5, 6 are coupled to each other. The contact surface 26 of the protrusions 25 is formed substantially perpendicular to an extension direction of the spacer 21, in order to be able to transmit forces as high as possible.

The clamping branches 23 project in a direction facing the connection bush 4 (i.e. radially inward with respect to the connection bush 4) beyond the rocker joint or connecting web 22 to form actuation branch portions 27. The actuation branch portions 27 and the clamping-branch portions 24 are rigidly connected to each other. When the actuation branch portions 27 are pressed/moved toward each other, preferably with only one hand, by a user, the clamping branches 23 are tilted about the connecting web 22 or the rocker joint, respectively, and the clamping-branch portions 24 move away from each other to be able to release a clamping engagement thereof with the access openings 9. The actuation branch portions 27 have a ribbing on the outside, which enables a safe, slip-free actuation of the actuation branch portions 27.

The connecting web 22 has side rims 28 which project laterally, i.e. in proximal and distal directions, beyond the clamping branches 22. A width of the connecting web 22 in this direction substantially corresponds to a distance between the support edges 10 of the second mounting coupling 6. In the connected state of the first and second mounting couplings 5, 6, the support edges 10 of the second mounting coupling 6 and the side rims 28 of the connecting web 22 are thus directly adjacent and in particular in abutment with each other when, as can be seen in FIG. 1, a longitudinal loading of the working channel 3 occurs. Lateral rims of the clamping-branch portions 24 oriented in proximal-distal direction do not come into contact with one side of the respective access opening 9, which improves the force transmission between the first and second mounting couplings 5, 6.

FIG. 1 and FIG. 4 show different configurations of the adaptive working channel apparatus with essentially the same design. In FIG. 1, two working channels 3 are connected to the second mounting coupling 6 at the same height relative to each other. In FIG. 4, the working channels 3 are arranged at longitudinally offset positions in a grid defined by the access openings 9.

Figure 5:
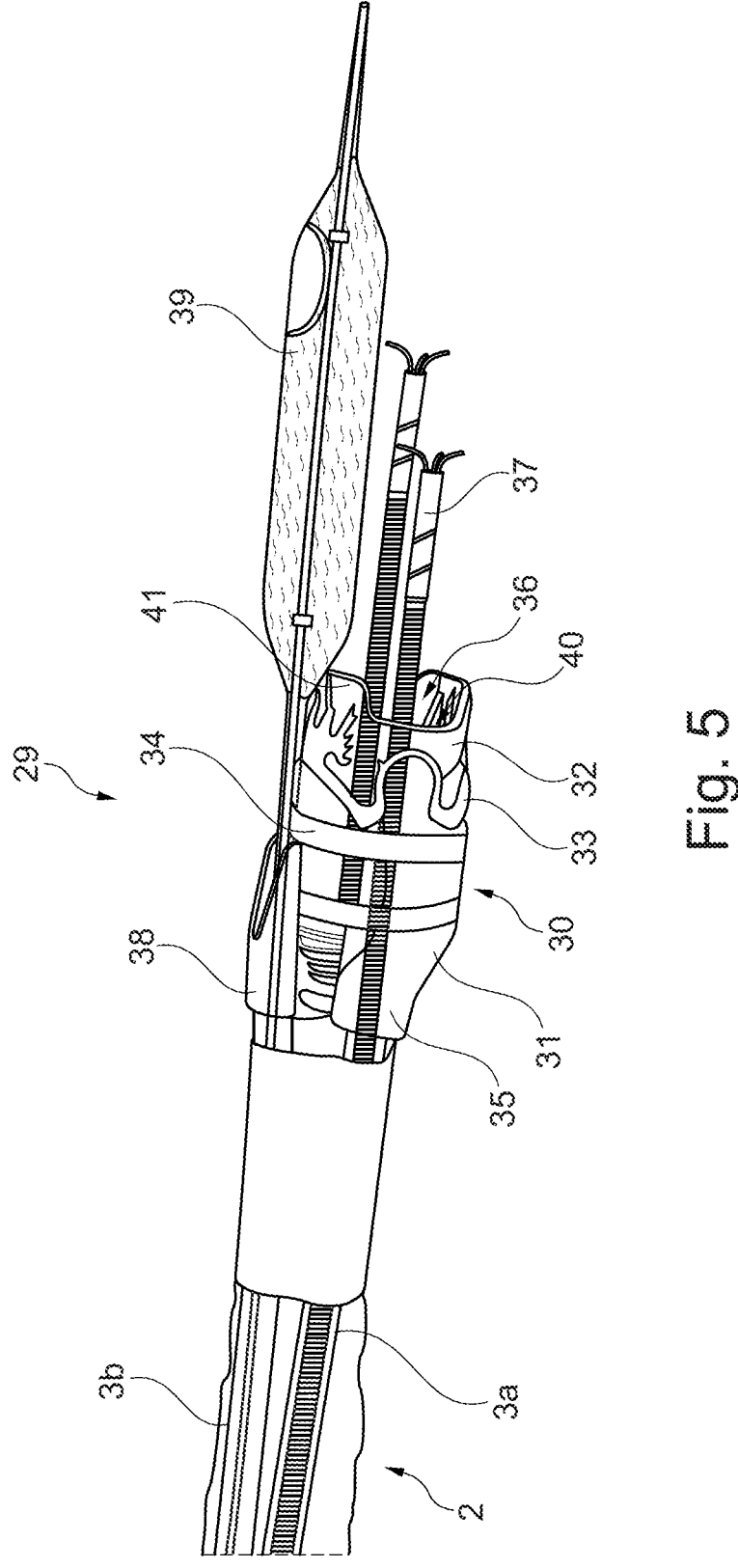
FIG. 5 shows an endoscope with a tissue-clip application adapter attached thereto according to a second aspect or a further embodiment.

FIG. 5 shows an endoscope 2, more specifically, an endoscope shaft having a tissue-clip application adapter 29 retrofitted to its distal endoscope head to add functionality to clip patient tissue to the endoscope 2. The tissue-clip application adapter 29 is provided in the form of a cap-like attachment and has a bush-shaped base body 30. The base body 30 has a proximal endoscope holding portion 31 configured for attachment to the endoscope head, and a tissue-clip holding portion 32 on which a tissue clip 33 is carried. Immediately proximal to the tissue clip 33 or the tissue-clip holding portion 32, respectively, a sliding bush 34 is mounted on the base body 30 to be longitudinally slidable. If the sliding bush 34 is moved in the distal direction, it contacts the tissue clip 33 and slides it distally off the tissue-clip application adapter 29.

A first adapter-integrated working-channel terminal 35 has a first inner channel formed for coupling with a first external working channel 3a. The first inner channel extends from a proximal direction from an outer side of the base body 30 in the distal direction and radially inward through a wall of the base body 30 and opens into an interior 36 of the base body 30. I.e., a proximal first channel end opens at an outer side of the base body 30 and a distal first channel end opens at an inner side of the base body 30. Preferably, a gripping instrument 37 is provided which is or can be inserted into the first working channel 3a to be advanced through the first inner channel into the interior 36 and, if applicable, distally out of the base body 30.

A second adapter-integrated working-channel terminal 38 has a second inner channel configured to couple to a second external working channel 3b. The second inner channel extends from a proximal direction along an outer side of the base body 30 in a distal direction. It opens to the outside of the base body 30 at a position proximal to the tissue-clip holding portion 32. I.e., both a proximal second channel end and a distal second channel end open at an outer side of the base body 30. Preferably, a spreading instrument 39, such as a balloon catheter, is provided which is or can be inserted into the second working channel 3a to be provided through the second working-channel terminal 38 outside the base body 30 and laterally adjacent to the tissue-clip holding portion 32.

The base body 30 furthermore has a distal front edge that includes two diametrically opposite recesses 40 extending in the proximal direction to allow folding of patient tissue pulled into the interior 36. Projections are provided between the recesses 40, the outer surfaces of which are formed as spread support surfaces 41 for holding open or respectively spreading the collapsible tissue clip 33. The tissue clip 33 has claw portions and is adapted to have these claw portions fold toward each other when the tissue clip 33 is pushed off the tissue clip holding portion 32. The claw portions are thus supported on the spread support surfaces 41. One of the spread support surfaces 41 is in particular arranged at a circumferential position at which the distal second channel end opens.

The first and second external working channels 3a, 3b are preferably external working channels 3 of an adaptable working channel apparatus 1 according to FIG. 1. Thus, the adaptable working channel apparatus 1 and the tissue-clip application adapter 29 according to FIG. 4 form a surgical equipping system, which in particular further comprises the gripping instrument 37 and the spreading instrument 39.

LIST OF REFERENCE SIGNS 1 adaptable working channel apparatus
2 endoscope
3 working channel
3a first external working channel of the surgical equipping system
3b second external working channel of the surgical equipping system
4 connection bush
5 first mounting coupling
6 second mounting coupling
7 handle-mounting sleeve
8 mounting rail
9 access opening/engagement element of the second mounting coupling
10 support edges
11 longitudinal gap
12 undercut/receiving opening
13 radial protrusion
14 strap holder
15 closure strap
16 strap fixing portion
17 closure portion
19 biopsy valve
20 Luer adapter
21 spacer/central bar
22 connecting web
23 clamping branches
24 clamping-branch portion
25 hook type protrusion/engagement element of the first mounting coupling
26 contact surface
27 actuation branch portion
28 Protruding side rim of the connecting web
29 tissue-clip application adapter
30 bush-like base body
31 proximal endoscope holding portion
32 tissue-clip holding portion
33 tissue clip
34 sliding bush
35 first adapter-integrated working-channel terminal
36 interior
37 gripping instrument
38 second adapter-integrated working-channel terminal
39 spreading instrument/balloon catheter
40 recesses of the distal front edge
41 spread support surfaces
The invention claimed is:

1. An adaptable working channel apparatus for adaptive mounting to an endoscope, the adaptable working channel apparatus comprising:

at least one external working channel connected at a proximal end portion to a first mounting coupling,
a handle-mounting sleeve formed separately from the at least one working channel and configured to encompass an endoscope shaft or an endoscope handle like a sleeve and having a radially outer circumferential side comprising at least a second mounting coupling which is configured to come into releasable mounting engagement with the first mounting coupling, wherein:
the first mounting coupling has two clamping branches spring-loaded into a clamping engagement, hinged together in a clothespin-like manner, to form a respective clamping branch portion and a manual actuation branch portion,
the second mounting coupling has a mounting rail extending in a longitudinal direction of the handle-mounting sleeve and has or forms at least one access opening which is dimensioned such that it can be form-fittingly embraced by the clamping branches of the first mounting coupling, and
the clamping branch portions each has an end section configured to engage a corresponding end section via the at least one access opening of the second mounting coupling when the first mounting coupling and the second mounting coupling are connected.

2. The adaptable working channel apparatus according to claim 1, wherein the clamping branches are respectively elastically connected to each other at a position between the clamping-branch portion and the actuation branch portion of the corresponding clamping branch via a connecting web that extends obliquely or perpendicularly to the clamping branches.

3. The adaptable working channel apparatus according to claim 2, wherein:
the connecting web is wider than the clamping branches such that it projects laterally beyond the clamping branches, and
the handle-mounting sleeve forms at least two support edges extending transversely to its longitudinal direction and spaced apart in the longitudinal direction, the distance between them corresponding to a width of the connecting web.

4. The adaptable working channel apparatus according to claim 1, wherein the first mounting coupling forms a connection bush having a respective distal end and a respective proximal end, and wherein the working channel is connected to the respective distal end and a Luer adapter or an integrated biopsy valve is formed at the respective proximal end.

5. An adaptable working channel apparatus for adaptive mounting to an endoscope, the adaptable working channel apparatus comprising:
at least one external working channel connected at a proximal end portion to a first mounting coupling,
a handle-mounting sleeve formed separately from the at least one working channel and configured to encompass an endoscope shaft or an endoscope handle like a sleeve and having a radially outer circumferential side comprising at least a second mounting coupling which is configured to come into releasable mounting engagement with the first mounting coupling, wherein:
the first mounting coupling has two clamping branches spring-loaded into a clamping engagement, hinged together in a clothespin-like manner, to form a respective clamping branch portion and a manual actuation branch portion, the second mounting coupling has a mounting rail extending in a longitudinal direction of the handle-mounting sleeve and has or forms at least one access opening which is dimensioned such that it can be form-fittingly embraced by the clamping branches of the first mounting coupling; and the mounting rail of the handle-mounting sleeve forms a plurality of undercuts that are arranged offset to each other in the longitudinal direction.

6. The adaptable working channel apparatus according to claim 1, wherein the handle-mounting sleeve forms a plurality of mounting rails that are arranged offset to each other in a circumferential direction of the handle-mounting sleeve.

7. The adaptable working channel apparatus according to claim 1, wherein the handle-mounting sleeve has a receiving opening configured to receive a radial protrusion of the endoscope shaft or of the endoscope handle.

8. The adaptable working channel apparatus according to claim 1, wherein the handle-mounting sleeve has a continuous longitudinal gap and is at least partially elastic, such that the handle-mounting sleeve can be snapped onto the endoscope handle or endoscope shaft in a clasp-like manner.

9. The adaptable working channel apparatus according to claim 8, wherein the handle-mounting sleeve comprises:

a strap holder to which a first end of a closure strap is attached or attachable, and a strap fixing portion configured to hold a closure portion of the closure strap in a position in which the closure strap is wrapped around the handle-mounting sleeve such that it extends across the longitudinal gap.

10. A tissue-clip application adapter configured in the manner of a cap attachment for the endoscope, the tissue-clip application adapter comprising:

a bush-like base body having a proximal endoscope holding portion configured to be attached to a distal head of the medical endoscope, and a tissue-clip holding portion configured to support a tissue clip on a radially outer circumferential surface such that a tissue clip is removable in the distal direction from the tissue-clip holding portion, a first adapter-integrated working-channel terminal having a first internal channel extending within the base body such that a proximal first channel end opens at an exterior of the base body and a distal first channel end opens at an interior within the base body, and a second adapter-integrated working-channel terminal having a second channel extending externally relative to and along the base body such that a proximal second channel end and a distal second channel end open at an outer side of the base body and that the distal second channel end is disposed proximal to the tissue-clip holding portion.

11. The tissue-clip application adapter according to claim 10, wherein a sliding bush is mounted in a longitudinally slidable manner on the base body immediately proximal to the tissue-clip holding portion for sliding the tissue clip distally off the tissue-clip holding portion.

12. The tissue-clip application adapter according to claim 10, wherein a distal front edge of the base body has two diametrically opposite recesses which extend in a proximal direction.

13. The tissue-clip application adapter according to claim 12, wherein the recesses are each arranged offset from the second adapter-integrated working-channel terminal in opposite circumferential directions of the base body.

14. The tissue-clip application adapter according to claim 10, wherein the tissue-clip holding portion forms two diametrically opposed spread support surfaces configured to hold the tissue clip spread open in a predetermined pose, wherein one of the spread support surfaces is disposed at an identical circumferential position of the base body as the second adapter-integrated working-channel terminal.

15. The tissue-clip application adapter according to claim 13, wherein the recesses are each arranged offset from the second adapter-integrated working-channel terminal in opposite circumferential directions of the base body by 70° to 110°.

16. A surgical equipping system for an endoscope, the surgical equipping system comprising:

an adaptable working channel apparatus for adaptive mounting to the endoscope, the adaptable working channel apparatus comprising:

at least one external working channel connected at a proximal end portion to a first mounting coupling, a handle-mounting sleeve formed separately from the at least one working channel and configured to encompass an endoscope shaft or an endoscope handle like a sleeve and having a radially outer circumferential side comprising at least a second mounting coupling which is configured to come into releasable mounting engagement with the first mounting coupling, wherein the first mounting coupling has two clamping branches spring-loaded into a clamping engagement, hinged together in a clothespin-like manner, to form a respective clamping branch portion and a manual actuation branch portion, and the second mounting coupling has a mounting rail extending in a longitudinal direction of the handle-mounting sleeve and has or forms at least one undercut which is dimensioned such that it can be form-fittingly embraced by the clamping branches of the first mounting coupling;

a tissue-clip application adapter configured in the manner of a cap attachment for the endoscope, the tissue-clip application adapter comprising:

a bush-like base body having a proximal endoscope holding portion configured to be attached to a distal head of the medical endoscope, and a tissue-clip holding portion configured to support a tissue clip on a radially outer circumferential surface such that a tissue clip is removable in the distal direction from the tissue-clip holding portion, a first adapter-integrated working-channel terminal having a first inner channel extending through the base body such that a proximal first channel end opens at an exterior of the base body and a distal first channel end opens at an interior within the base body, and a second adapter-integrated working-channel terminal having a second inner channel extending along the base body such that a proximal second channel end and a distal second channel end open at an outer side of the base body and that the distal second channel end is disposed proximal to the tissue-clip holding portion, wherein the first adapter-integrated working-channel terminal is coupled to a distal end portion of the external working channel of the adaptable working channel apparatus as a first external working channel;

a gripping instrument inserted or configured to be inserted distally through the first external working channel so as to be advanceable through the interior of the base body of the tissue-clip application adapter, a second external working channel having a third mounting coupling at a respective proximal end portion for mounting to the handle-mounting sleeve of the adaptable working channel apparatus and having a respective distal end portion coupled to the second adapter-integrated working-channel terminal of the tissue-clip application adapter; and a spreading instrument which is inserted or configured to be inserted into the second external working channel in a distal direction to be providable radially outside the base body of the tissue-clip application adapter.

17. The adaptable working channel apparatus according to claim 1, wherein the end section of the clamping branch portions comprises a hook-shaped protrusion having a contact surface.

18. The adaptable working channel apparatus according to claim 1, wherein the contact surface of the protrusion is configured to contact a corresponding contact surface of the at least one access opening when the first mounting coupling and second mounting coupling are connected to each other.

19. The adaptable working channel apparatus according to claim 1, wherein the contact surface of the protrusions extends along an axis perpendicular to an extension direction of a spacer extending radially outward relative to the at least one external working channel.

*     *     *     *     *